United States Patent
Stahmann et al.

(10) Patent No.: US 6,553,258 B2
(45) Date of Patent: Apr. 22, 2003

(54) SYSTEM AND METHOD FOR MANAGING REFRACTORY PERIODS IN A CARDIAC RHYTHM MANAGEMENT DEVICE WITH BIVENTRICULAR SENSING

(75) Inventors: Jeffrey E. Stahmann, Ramsey, MN (US); Andrew P. Kramer, Stillwater, MN (US); James O. Gilkerson, Stillwater, MN (US); Lorenzo DiCarlo, Minneapolis, MN (US); Rene H. Wentkowski, White Bear Lake, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 71 days.

(21) Appl. No.: 09/748,733

(22) Filed: Dec. 26, 2000

(65) Prior Publication Data

US 2002/0082653 A1 Jun. 27, 2002

(51) Int. Cl.⁷ .............................................. A61N 1/368
(52) U.S. Cl. ............................................ 607/9; 607/15
(58) Field of Search ............................. 607/9, 15, 148

(56) References Cited

U.S. PATENT DOCUMENTS

| | | | |
|---|---|---|---|
| 4,343,311 A | * 8/1982 | Markowitz | 607/9 |
| 4,354,497 A | 10/1982 | Kahn | 128/419 D |
| 4,515,161 A | * 5/1985 | Wittkampf et al. | 607/27 |
| 4,686,989 A | 8/1987 | Smyth et al. | 128/419 PG |
| 4,779,617 A | 10/1988 | Whigham | 128/419 P |
| 4,928,688 A | 5/1990 | Mower | 128/419 PG |
| 4,974,589 A | * 12/1990 | Sholder | 607/9 |
| 5,103,820 A | 4/1992 | Markowtiz | 128/419 PG |
| 5,123,412 A | 6/1992 | Betzold | 128/419 PG |
| 5,129,393 A | 7/1992 | Brumwell | 128/419 PG |
| 5,156,149 A | 10/1992 | Hudrlik | 128/419 PG |
| 5,174,289 A | 12/1992 | Cohen | 128/419 PG |
| 5,233,985 A | 8/1993 | Hudrlik | 607/27 |
| 5,267,560 A | 12/1993 | Cohen | 607/25 |
| 5,366,488 A | 11/1994 | Franberg et al. | 607/9 |
| 5,370,665 A | 12/1994 | Hudrlik | 607/9 |
| 5,514,161 A | 5/1996 | Limousin | 607/9 |
| 5,522,857 A | 6/1996 | van Krieken | 607/9 |
| 5,584,867 A | 12/1996 | Limousin et al. | 607/9 |
| 5,591,214 A | 1/1997 | Lu | 607/9 |
| 5,653,738 A | 8/1997 | Sholder | 607/14 |
| 5,674,259 A | 10/1997 | Gray | 607/20 |
| 5,776,167 A | 7/1998 | Levine et al. | 607/9 |
| 5,792,203 A | * 8/1998 | Schroeppel | 607/30 |
| 5,797,970 A | 8/1998 | Pouvreau | 607/9 |
| 5,935,160 A | 8/1999 | Auricchio et al. | 607/122 |
| 5,941,830 A | 8/1999 | Williams | 600/509 |
| 6,148,234 A | * 11/2000 | Struble | 607/11 |

* cited by examiner

Primary Examiner—Kennedy Schaetzle
(74) Attorney, Agent, or Firm—Schwegman, Lundberg, Woessner & Kluth, P.A.

(57) ABSTRACT

A method and system for managing refractory periods in a cardiac rhythm management device configured for biventricular or biatrial sensing. Refractory periods for each channel of the pacemaker are provided by interval timers that are triggered by sensed or paced events in order to prevent misinterpretation of sensing signals.

33 Claims, 9 Drawing Sheets

SYSTEM AND METHOD FOR MANAGING REFRACTORY PERIODS IN A CARDIAC RHYTHM MANAGEMENT DEVICE WITH BIVENTRICULAR SENSING

FIELD OF THE INVENTION

This invention pertains to methods and systems for operating a cardiac rhythm management device. In particular, the invention relates to defining and managing periods during which sensing channels of the device are rendered refractory.

BACKGROUND

Cardiac rhythm management devices are implantable devices that provide electrical stimulation to selected chambers of the heart in order to treat disorders of cardiac rhythm. A pacemaker, for example, is a cardiac rhythm management device that paces the heart with timed pacing pulses. The most common condition for which pacemakers are used is in the treatment of bradycardia, where the ventricular rate is too slow. Atrio-ventricular conduction defects (i.e., AV block) that are fixed or intermittent and sick sinus syndrome represent the most common causes of bradycardia for which permanent pacing may be indicated. If functioning properly, the pacemaker makes up for the heart's inability to pace itself at an appropriate rhythm in order to meet metabolic demand by enforcing a minimum heart rate. Pacing therapy may also be applied in order to treat cardiac rhythms that are too fast, termed anti-tachycardia pacing. (As the term is used herein, a pacemaker is any cardiac rhythm management device with a pacing functionality, regardless of any other functions it may perform such as cardioversion or defibrillation.)

Also included within the concept of cardiac rhythm is the degree to which the heart chambers contract in a coordinated manner during a cardiac cycle to result in the efficient pumping of blood. The heart has specialized conduction pathways in both the atria and the ventricles that enable the rapid conduction of excitation (i.e., depolarization) throughout the myocardium. These pathways conduct excitatory impulses from the sino-atrial node to the atrial myocardium, to the atrio-ventricular node, and thence to the ventricular myocardium to result in a coordinated contraction of both atria and both ventricles. This both synchronizes the contractions of the muscle fibers of each chamber and synchronizes the contraction of each atrium or ventricle with the contralateral atrium or ventricle. Without the synchronization afforded by the normally functioning specialized conduction pathways, the heart's pumping efficiency is greatly diminished. Patients who exhibit pathology of these conduction pathways, such as bundle branch blocks, can thus suffer compromised cardiac output.

Patients with conventional pacemakers can also have compromised cardiac output because artificial pacing with an electrode fixed into an area of the myocardium does not take advantage of the above-described specialized conduction system. This is because the specialized conduction system can only be entered by impulses emanating from the sino-atrial or atrio-ventricular nodes. The spread of excitation from a single pacing site must proceed only via the much slower conducting muscle fibers of either the atria or the ventricles, resulting in the part of the myocardium stimulated by the pacing electrode contracting well before parts of the chamber located more distally to the electrode, including the myocardium of the chamber contralateral to the pacing site. Although the pumping efficiency of the heart is somewhat reduced from the optimum, most patients can still maintain more than adequate cardiac output with artificial pacing.

Heart failure is clinical syndrome in which an abnormality of cardiac function causes cardiac output to fall below a level adequate to meet the metabolic demand of peripheral tissues and is usually referred to as congestive heart failure (CHF) due to the accompanying venous and pulmonary congestion. CHF can be due to a variety of etiologies with ischemic heart disease being the most common. Some CHF patients suffer from some degree of AV block or are chronotropically deficient such that their cardiac output can be improved with conventional bradycardia pacing. Such pacing, however, may result in some degree of uncoordination in atrial and/or ventricular contractions due to the way in which pacing excitation is spread throughout the myocardium as described above. The resulting diminishment in cardiac output may be significant in a CHF patient whose cardiac output is already compromised. Intraventricular and/or interventricular conduction defects (e.g., bundle branch blocks) are also commonly found in CHF patients. In order to treat these problems, cardiac rhythm management devices have been developed which provide pacing stimulation to one or more heart chambers in an attempt to improve the coordination of atrial and/or ventricular contractions, termed cardiac resynchronization therapy.

In conventional pacemakers with sensing channels for sensing one or more heart chambers, the ventricular and/or atrial sensing channels are rendered refractory following certain events, such that certain sensed events are ignored for the duration of the period. Sensing channels are rendered refractory both in order to prevent reentry into the system of an output pacing pulse (in which case the sensing amplifiers are blanked) and to prevent the misinterpretation of input data by the sensing of after potentials or by crosstalk between sensing channels. Cardiac resynchronization therapy may involve pacing both atria, both ventricles, or a heart chamber at one or more pacing sites based upon senses from another site. In order to control the pacing and avoid pacing a chamber or site in the presence of intrinsic activity, sensing channels should be provided for each chamber or site. Sensing both ventricles or both atria, however, requires that refractory periods be managed differently from the situation where only one atria or one ventricle is sensed.

SUMMARY OF THE INVENTION

The present invention is a system and method for managing the refractory periods of sensing channels in a cardiac rhythm management device in which both ventricles, both atria, and/or multiple sites in the same heart chamber are sensed. Such sensing configurations can most usefully be employed in delivering cardiac resynchronization therapy. The refractory periods for the sensing channels are managed in a manner such that misinterpretation of sense signals is avoided while still allowing the device to pace one or more chambers safely and at the appropriate times.

In an exemplary cardiac resynchronization pacing configuration, heart chambers designated as a rate chamber and a synchronized chamber are sensed through separate channels, and at least one chamber is paced upon expiration of an escape interval without receipt of a rate chamber sense signal. In accordance with the invention, each sensing channel is rendered refractory for a separately selected pacing refractory period after a pacing event, and a sensing channel is rendered refractory for a selected sensing refractory period after receipt of a sense signal from that channel while leaving the other channel non-refractory.

In a particular embodiment of the invention, the rate and synchronized chambers are the right and left ventricles, respectively, and an atrial sensing and pacing channel is also present. The atrial sensing channel may be rendered refractory for selected intervals following an atrial sense, an atrial pace, a pace of either ventricle, or a right ventricular sense signal.

DESCRIPTION OF THE INVENTION

The present invention relates to a method and system for managing refractory periods for multiple sensing channels in order to safely and effectively implement a synchronized pacing mode. As will be described below, such modes may be used to deliver cardiac resynchronization therapy.

1. Hardware Platform

Pacemakers are typically implanted subcutaneously or submuscularly and have leads threaded intravenously into the heart to connect the device to electrodes used for sensing and pacing. A programmable electronic controller causes the pacing pulses to be output in response to lapsed time intervals and sensed electrical activity (i.e., intrinsic heart beats not as a result of a pacing pulse). Pacemakers sense intrinsic cardiac electrical activity by means of internal electrodes disposed within or near the chamber to be sensed. A depolarization wave associated with an intrinsic contraction of the atria or ventricles that is detected by the pacemaker is referred to as an atrial sense or ventricular sense, respectively. In order to cause such a contraction in the absence of an intrinsic beat, a pacing pulse (either an atrial pace or a ventricular pace) with energy above a certain pacing threshold is delivered to the chamber.

Figure 1:
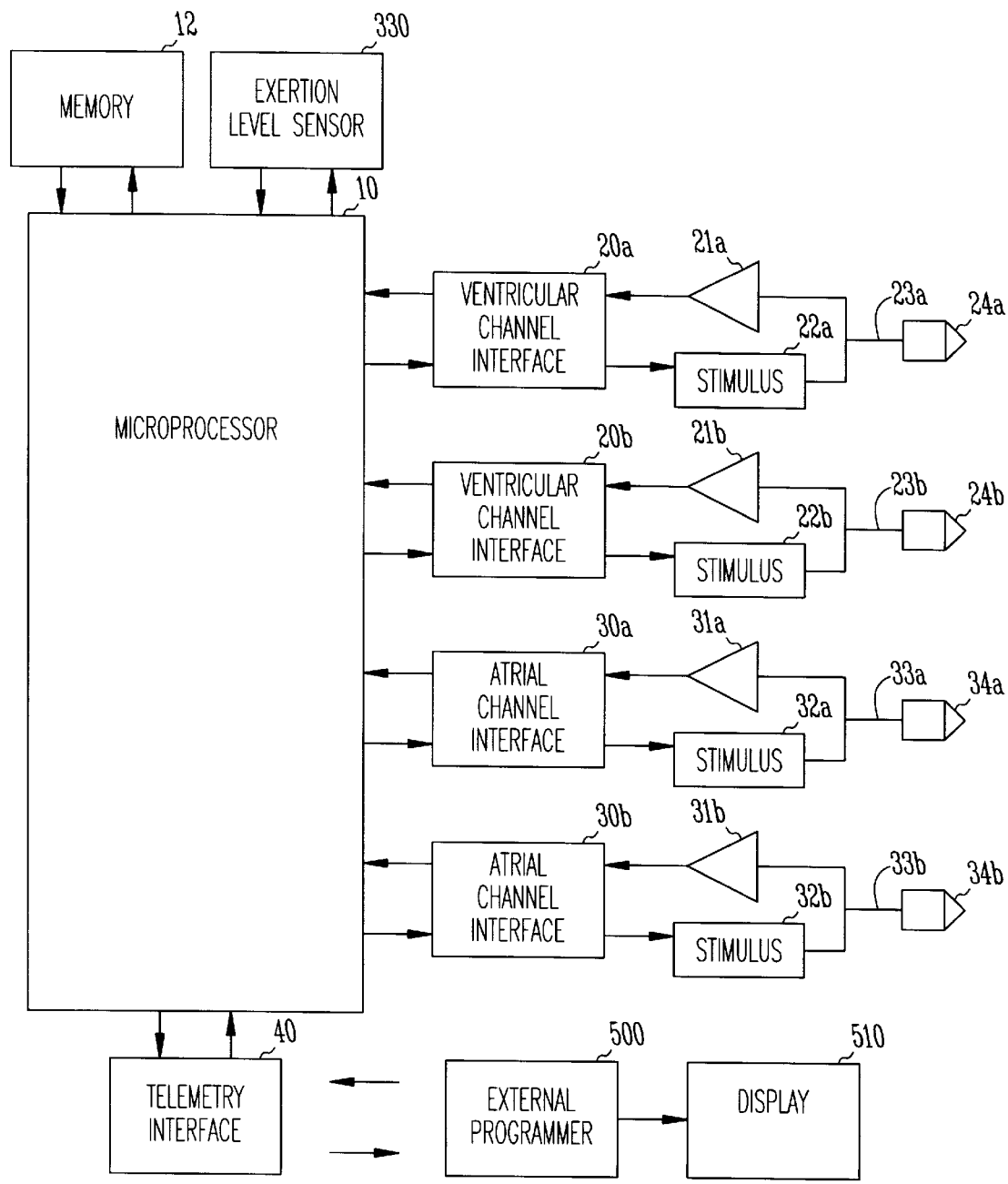
FIG. 1 is a system diagram of a pacemaker configured for biventricular pacing and sensing.

FIG. 1 shows a system diagram of a microprocessor-based pacemaker physically configured with sensing and pacing channels for both atria and both ventricles. The controller 10 of the pacemaker is a microprocessor which communicates with a memory 12 via a bidirectional data bus. The memory 12 typically comprises a ROM (read-only memory) for program storage and a RAM (random-access memory) for data storage. The pacemaker has atrial sensing and pacing channels comprising electrode 34a–b, leads 33a–b, sensing amplifiers 31a–b, pulse generators 32a–b, and atrial channel interfaces 30a–b which communicate bidirectionally with microprocessor 10. The device also has ventricular sensing and pacing channels for both ventricles comprising electrodes 24a–b, leads 23a–b, sensing amplifiers. 21a–b, pulse generators 22a–b, and ventricular channel interfaces 20a–b. In the figure, "a" designates one ventricular or atrial channel and "b" designates the channel for the contralateral chamber. In this embodiment, a single electrode is used for sensing and pacing in each channel, known as a unipolar lead. Other embodiments may employ bipolar leads which include two electrodes for outputting a pacing pulse and/or sensing intrinsic activity. The channel interfaces 20a–b and 30a–b include analog-to-digital converters for digitizing sensing signal inputs from the sensing amplifiers and registers which can be written to by the microprocessor in order to output pacing pulses, change the pacing pulse amplitude, and adjust the gain and threshold values for the sensing amplifiers. An exertion level sensor 330 (e.g., an accelerometer or a minute ventilation sensor) enables the controller to adapt the pacing rate in accordance with changes in the patient's physical activity. A telemetry interface 40 is also provided for communicating with an external programmer 500 which has an associated display 510. A pacemaker incorporating the present invention may possess all of the components in FIG. 1 and be programmable so as to operate in a number of different modes, or it may have only those components necessary to operate in a particular mode.

The controller 10 controls the overall operation of the device in accordance with programmed instructions stored in memory. The controller 10 controls the delivery of paces via the pacing channels, interprets sense signals from the sensing channels, implements timers for defining escape intervals and sensory refractory periods, and performs the pace counting functions as described below. It should be appreciated, however, that these functions could also be performed by custom logic circuitry either in addition to or instead of a programmed microprocessor.

2. Bradycardia Pacing Modes

Bradycardia pacing modes refer to pacing algorithms used to pace the atria and/or ventricles when the intrinsic ventricular rate is inadequate either due to AV conduction blocks or sinus node dysfunction. Such modes may either be single-chamber pacing, where either an atrium or a ventricle is paced, or dual-chamber pacing in which both an atrium and a ventricle are paced. The modes are generally designated by a letter code of three positions where each letter in the code refers to a specific function of the pacemaker. The first letter refers to which heart chambers are paced and which may be an A (for atrium), a V (for ventricle), D (for both chambers), or O (for none). The second letter refers to which chambers are sensed by the pacemaker's sensing channels and uses the same letter designations as used for pacing. The third letter refers to the pacemaker's response to a sensed P wave from the atrium or an R wave from the ventricle and may be an I (for inhibited), T (for triggered), D (for dual in which both triggering and inhibition are used), and O (for no response). Modern pacemakers are typically programmable so that they can operate in any mode which the physical configuration of the device will allow. Additional sensing of physiological data allows some pacemakers to change the rate at which they pace the heart in accordance with some parameter correlated to metabolic demand. Such pacemakers are called rate-adaptive pacemakers and are designated by a fourth letter added to the three-letter code, R.

Pacemakers can enforce a minimum heart rate either asynchronously or synchronously. In asynchronous pacing, the heart is paced at a fixed rate irrespective of intrinsic cardiac activity. There is thus a risk with asynchronous pacing that a pacing pulse will be delivered coincident with an intrinsic beat and during the heart's vulnerable period which may cause fibrillation. Most pacemakers for treating bradycardia today are therefore programmed to operate synchronously in a so-called demand mode where sensed cardiac events occurring within a defined interval either trigger or inhibit a pacing pulse. Inhibited demand pacing modes utilize escape intervals to control pacing in accordance with sensed intrinsic activity. In an inhibited demand mode, a pacing pulse is delivered to a heart chamber during a cardiac cycle only after expiration of a defined escape interval during which no intrinsic beat by the chamber is detected. If an intrinsic beat occurs during this interval, the heart is thus allowed to "escape" from pacing by the pacemaker. Such an escape interval can be defined for each paced chamber. For example, a ventricular escape interval can be defined between ventricular events so as to be restarted with each ventricular sense or pace. The inverse of this escape interval is the minimum rate at which the pacemaker will allow the ventricles to beat, sometimes referred to as the lower rate limit (LRL).

In atrial tracking pacemakers (i.e., VDD or DDD mode), another ventricular escape interval is defined between atrial and ventricular events, referred to as the atrio-ventricular interval (AVI). The atrio-ventricular interval is triggered by an atrial sense or pace and stopped by a ventricular sense or pace. A ventricular pace is delivered upon expiration of the atrio-ventricular interval if no ventricular sense occurs before. Atrial-tracking ventricular pacing attempts to maintain the atrio-ventricular synchrony occurring with physiological beats whereby atrial contractions augment diastolic filling of the ventricles. If a patient has a physiologically normal atrial rhythm, atrial-tracking pacing also allows the ventricular pacing rate to be responsive to the metabolic needs of the body.

A pacemaker can also be configured to pace the atria on an inhibited demand basis. An atrial escape interval is then defined as the maximum time interval in which an atrial sense must be detected after a ventricular sense or pace before an atrial pace will be delivered. When atrial inhibited demand pacing is combined with atrial-triggered ventricular demand pacing (i.e., DDD mode), the lower rate limit interval is then the sum of the atrial escape interval and the atrio-ventricular interval.

Another type of synchronous pacing is atrial-triggered or ventricular-triggered pacing. In this mode, an atrium or ventricle is paced immediately after an intrinsic beat is detected in the respective chamber. Triggered pacing of a heart chamber is normally combined with inhibited demand pacing so that a pace is also delivered upon expiration of an escape interval in which no intrinsic beat occurs. Such triggered pacing may be employed as a safer alternative to asynchronous pacing when, due to far-field sensing of electromagnetic interference from external sources or skeletal muscle, false inhibition of pacing pulses is a problem. If a sense in the chamber's sensing channel is an actual depolarization and not a far-field sense, the triggered pace is delivered during the chamber's physiological refractory period and is of no consequence.

3. Cardiac Resynchronization Therapy

Cardiac resynchronization therapy is pacing stimulation applied to one or more heart chambers in a mariner that restores or maintains synchronized bilateral contractions of the atria and/or ventricles and thereby improves pumping efficiency. Certain patients with conduction abnormalities may experience improved cardiac synchronization with conventional single-chamber or dual-chamber pacing as described above. For example, a patient with left bundle branch block may have a more coordinated contraction of the ventricles with a pace than as a result of an intrinsic contraction. In that sense, conventional bradycardia pacing of an atrium and/or a ventricle may be considered as resynchronization therapy. Resynchronization pacing, however, may also involve pacing both ventricles and/or both atria in accordance with a synchronized pacing mode as described below. A single chamber may also be resynchronized to compensate for intra-atrial or intra-ventricular conduction delays by delivering paces to multiple sites of the chamber.

It is advantageous to deliver resynchronization therapy in conjunction with one or more synchronous bradycardia pacing modes, such as are described above. One atrial and/or one ventricular pacing sites are designated as rate sites, and paces are delivered to the rate sites based upon pacing and sensed intrinsic activity at the site in accordance with the bradycardia pacing mode. In a single-chamber bradycardia pacing mode, for example, one of the paired atria or one of the ventricles is designated as the rate chamber. In a dual-chamber bradycardia pacing mode, either the right or left atrium is selected as the atrial rate chamber and either the right or left ventricle is selected as the ventricular rate chamber. The heart rate and the escape intervals for the pacing mode are defined by intervals between sensed and paced events in the rate chambers only. Resynchronization therapy may then be implemented by adding synchronized pacing to the bradycardia pacing mode where paces are delivered to one or more synchronized pacing sites in a defined time relation to one or more selected sensing and pacing events that either reset escape intervals or trigger paces in the bradycardia pacing mode. Multiple synchronized sites may be paced through multiple synchronized sensing/pacing channels, and the multiple synchronized sites may be in the same or different chambers as the rate site.

In bilateral synchronized pacing, which may be either biatrial or biventricular synchronized pacing, the heart chamber contralateral to the rate chamber is designated as a synchronized chamber. For example, the right ventricle may be designated as the rate ventricle and the left ventricle designated as the synchronized ventricle, and the paired atria may be similarly designated. Each synchronized chamber is then paced in a timed relation to a pace or sense occurring in the contralateral rate chamber.

One synchronized pacing mode may be termed offset synchronized pacing. In this mode, the synchronized chamber is paced with a positive, negative, or zero timing offset as measured from a pace delivered to its paired rate chamber, referred to as the synchronized chamber offset interval. The offset interval may be zero in order to pace both chambers simultaneously, positive in order to pace the synchronized chamber after the rate chamber, or negative to pace the synchronized chamber before the rate chamber. One example of such pacing is biventricular offset synchronized pacing where both ventricles are paced with a specified offset interval. The rate ventricle is paced in accordance with a synchronous bradycardia mode which may include atrial tracking, and the ventricular escape interval is reset with either a pace or a sense in the rate ventricle. (Resetting in this context refers to restarting the interval in the case of an LRL ventricular escape interval and to stopping the interval in the case of an AVI.) Thus, a pair of ventricular paces are delivered after expiration of the AVI escape interval or expiration of the LRL escape interval, with ventricular pacing inhibited by a sense in the rate ventricle that restarts the LRL escape interval and stops the AVI escape interval. In this mode, the pumping efficiency of the heart will be increased in some patients by simultaneous pacing of the ventricles with an offset of zero. However, it may be desirable in certain patients to pace one ventricle before the other in order to compensate for different conduction velocities in the two ventricles, and this may be accomplished by specifying a particular positive or negative ventricular offset interval.

Another synchronized mode is triggered synchronized pacing. In one type of triggered synchronized pacing, the synchronized chamber is paced after a specified trigger interval following a sense in the rate chamber, while in another type the rate chamber is paced after a specified trigger interval following a sense in the synchronized chamber. The two types may also be employed simultaneously. For example, with a trigger interval of zero, pacing of one chamber is triggered to occur in the shortest time possible after a sense in the other chamber in order to produce a coordinated contraction. (The shortest possible time for the triggered pace is limited by a sense-to-pace latency period dictated by the hardware.) This mode of pacing may be desirable when the intra-chamber conduction time is long enough that the pacemaker is able to reliably insert a pace before depolarization from one chamber reaches the other. Triggered synchronized pacing can also be combined with offset synchronized pacing such that both chambers are paced with the specified offset interval if no intrinsic activity is sensed in the rate chamber and a pace to the rate chamber is not otherwise delivered as a result of a triggering event. A specific example of this mode is ventricular triggered synchronized pacing where the rate and synchronized chambers are the right and left ventricles, respectively, and a sense in the right ventricle triggers a pace to the left ventricle and/or a sense in the left ventricle triggers a pace to the right ventricle.

As with other synchronized pacing modes, the rate chamber in a triggered synchronized pacing mode can be paced with one or more synchronous bradycardia pacing modes. If the rate chamber is controlled by a triggered bradycardia mode, a sense in the rate chamber sensing channel, in addition to triggering a pace to the synchronized chamber, also triggers an immediate rate chamber pace and resets any rate chamber escape interval. The advantage of this modal combination is that the sensed event in the rate chamber sensing channel might actually be a far-field sense from the synchronized chamber, in which case the rate chamber pace should not be inhibited. In a specific example, the right and left ventricles are the rate and synchronized chambers, respectively, and a sense in the right ventricle triggers a pace to the left ventricle. If right ventricular triggered pacing is also employed as a bradycardia mode, both ventricles are paced after a right ventricular sense has been received to allow for the possibility that the right ventricular sense was actually a far-field sense of left ventricular depolarization in the right ventricular channel. If the right ventricular sense were actually from the right ventricle, the right ventricular pace would occur during the right ventricle's physiological refractory period and cause no harm.

As mentioned above, certain patients may experience some cardiac resynchronization from the pacing of only one ventricle and/or one atrium with a conventional bradycardia pacing mode. It may be desirable, however, to pace a single atrium or ventricle in accordance with a pacing mode based upon senses from the contralateral chamber. This mode, termed synchronized chamber-only pacing, involves pacing only the synchronized chamber based upon senses from the rate chamber. One way to implement synchronized chamber-only pacing is to pseudo-pace the rate chamber whenever the synchronized chamber is paced before the rate chamber is paced, such that the pseudo-pace inhibits a rate chamber pace and resets any rate chamber escape intervals. Such pseudo-pacing can be combined with the offset synchronized pacing mode using a negative offset to pace the synchronized chamber before the rate chamber and thus pseudo-pace the rate chamber, which inhibits the real scheduled rate chamber pace and resets the rate chamber pacing escape intervals. One advantage of this combination is that sensed events in the rate chamber will inhibit the synchronized chamber-only pacing, which may benefit some patients by preventing pacing that competes with intrinsic activation (i.e., fusion beats). Another advantage of this combination is that rate chamber pacing can provide backup pacing when in a synchronized chamber-only pacing mode, such that when the synchronized chamber pace is prevented, for example to avoid pacing during the chamber vulnerable period following a prior contraction, the rate chamber will not be pseudo-paced and thus will be paced upon expiration of the rate chamber escape interval. Synchronized chamber-only pacing can be combined also with a triggered synchronized pacing mode, in particular with the type in which the synchronized chamber is triggered by a sense in the rate chamber. One advantage of this combination is that sensed events in the rate chamber will trigger the synchronized chamber-only pacing, which may benefit some patients by synchronizing the paced chamber contractions with premature contralateral intrinsic contractions.

An example of synchronized chamber-only pacing is left ventricle-only synchronized pacing where the rate and synchronized chambers are the right and left ventricles, respectively. Left ventricle-only synchronized pacing may be advantageous where the conduction velocities within the ventricles are such that pacing only the left ventricle results in a more coordinated contraction by the ventricles than with conventional right ventricular pacing or biventricular pacing. Left ventricle-only synchronized pacing may be implemented in inhibited demand modes with or without atrial tracking, similar to biventricular pacing. A left ventricular pace is then delivered upon expiration of the AVI escape interval or expiration of the LRL escape interval, with left ventricular pacing inhibited by a right ventricular sense that restarts the LRL escape interval and stops the AVI escape interval.

In the synchronized modes described above, the rate chamber is synchronously paced with a mode based upon detected intrinsic activity in the rate chamber, thus protecting the rate chamber against paces being delivered during the vulnerable period. In order to provide similar protection to a synchronized chamber or synchronized pacing site, a synchronized chamber protection period (SCPP) may be provided. (In the case of multi-site synchronized pacing, a similar synchronized site protection period may be provided for each synchronized site.) The SCPP is a programmed interval which is initiated by sense or pace occurring in the synchronized chamber during which paces to the synchronized chamber are inhibited. For example, if the right ventricle is the rate chamber and the left ventricle is the synchronized chamber, a left ventricular protection period LVPP is triggered by a left ventricular sense which inhibits a left ventricular pace which would otherwise occur before the escape interval expires. The SCPP may be adjusted dynamically as a function of heart rate and may be different depending upon whether it was initiated by a sense or a pace. The SCPP provides a means to inhibit pacing of the synchronized chamber when a pace might be delivered during the vulnerable period or when it might compromise pumping efficiency by pacing the chamber too close to an intrinsic beat. In the case of a triggered mode where a synchronized chamber sense triggers a pace to the synchronized chamber, the pacing mode may be programmed to ignore the SCPP during the triggered pace. Alternatively, the mode may be programmed such that the SCPP starts only after a specified delay from the triggering event, which allows triggered pacing but prevents pacing during the vulnerable period.

In the case of synchronized chamber-only synchronized pacing, a synchronized chamber pace may be inhibited if a synchronized chamber sense occurs within a protection period prior to expiration of the rate chamber escape interval. Since the synchronized chamber pace is inhibited by the protection period, the rate chamber is not pseudo-paced and, if no intrinsic activity is sensed in the rate chamber, it will be paced upon expiration of the rate chamber escape intervals. The rate chamber pace in this situation may thus be termed a safety pace. For example, in left ventricle-only synchronized pacing, a right ventricular safety pace is delivered if the left ventricular pace is inhibited by the left ventricular protection period and no right ventricular sense has occurred.

As noted above, synchronized pacing may be applied to multiple sites in the same or different chambers. The synchronized pacing modes described above may be implemented in a multi-site configuration by designating one sensing/pacing channel as the rate channel for sensing/pacing a rate site, and designating the other sensing/pacing channels in either the same or the contralateral chamber as synchronized channels for sensing/pacing one or more synchronized sites. Pacing and sensing in the rate channel then follows rate chamber timing rules, while pacing and sensing in the synchronized channels follows synchronized chamber timing rules as described above. The same or different synchronized pacing modes may be used in each synchronized channel.

4. Refractory Period Management

The present invention is a system and method for managing refractory periods. A refractory period is an interval during which sensed activity from a sensing channel neither inhibits nor triggers a pacing pulse. However, sensed events during the refractory period are often used for other device algorithms such as those used to detect atrial arrhythmias and those used to extend the refractory period in the presence of persistent electromagnetic interference.

Refractory periods are often implemented using a blanking interval. When used, the blanking interval usually constitutes the first part of the refractory period. During the blanking interval, the device ignores all electrical activity sensed by the sensing channel. Blanking intervals can shield the sensing channel from pacing artifacts or cross-chamber depolarization effects. Refractory periods are also often implemented using a retriggerable noise interval, where the noise interval often constitutes the last part of the refractory period. Sensed events occurring within the noise interval will restart the noise interval, thus increasing the length of the refractory period.

The following description of the invention dealing with refractory period management is set forth with respect to an exemplary cardiac rhythm management device that provides ventricular pacing in a synchronized mode and in which the rate and synchronized chambers are the right and left ventricles, respectively. It should be appreciated, however, that similar embodiments could be constructed in accordance with the description by replacing the right and left ventricles with other heart chambers or cardiac sites designated as rate and synchronized chambers.

The exemplary device provides sensing/pacing channels for an atrium and both ventricles. FIGS. 2–18 depict cardiac events and illustrate the refractory periods for the sensing channels. Such refractory periods may be provided by timers implemented in hardware or software executed by the controller in FIG. 1. Each refractory period is defined by its sensing channel and the particular cardiac or pacemaker event that triggers it. Refractory periods following sensed (i.e., intrinsic) or paced events will be referred to as sensing or pacing refractory periods, respectively.

Figure 2:
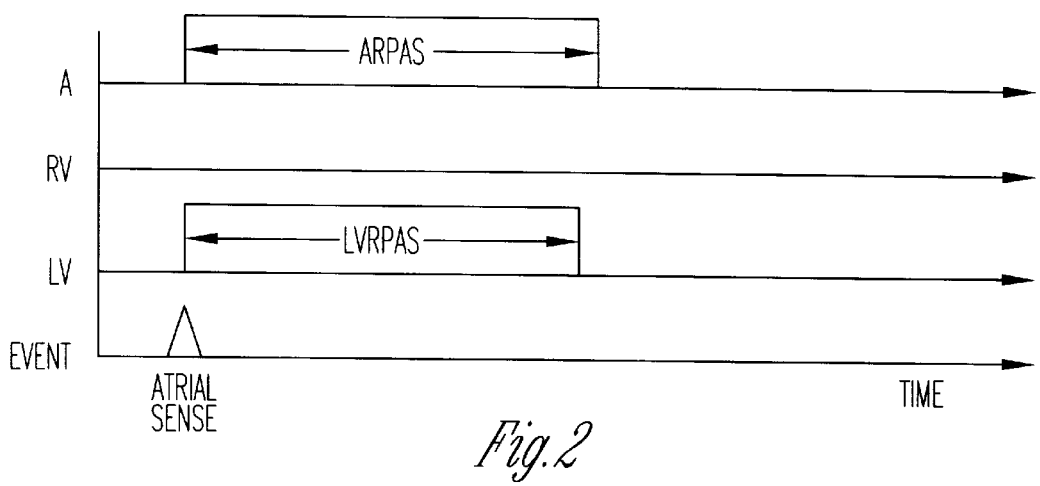
FIG. 2 shows refractory periods following a sensed atrial event.

FIG. 2 shows the refractory periods of the atrial and both right and left ventricular channels after a sensed atrial event. The atrial channel is rendered refractory for a selected interval ARPAS which prevents any electrical events occurring after the atrial depolarization and before expiration of the interval from being interpreted as an atrial sense. The right ventricular channel continues normal sensing as with conventional pacemakers since far-field sensing of the atrium by a right ventricular electrode is unlikely. A refractory period for the left ventricular channel may be necessary, however. Since a left ventricular electrode is normally placed via the coronary sinus, it may be placed rather high in the ventricle in close proximity to the left atrium. In order to prevent oversensing of the left atrium by the left ventricular channel, the channel can be made refractory for a selected interval LVRPAS.

Figure 3:
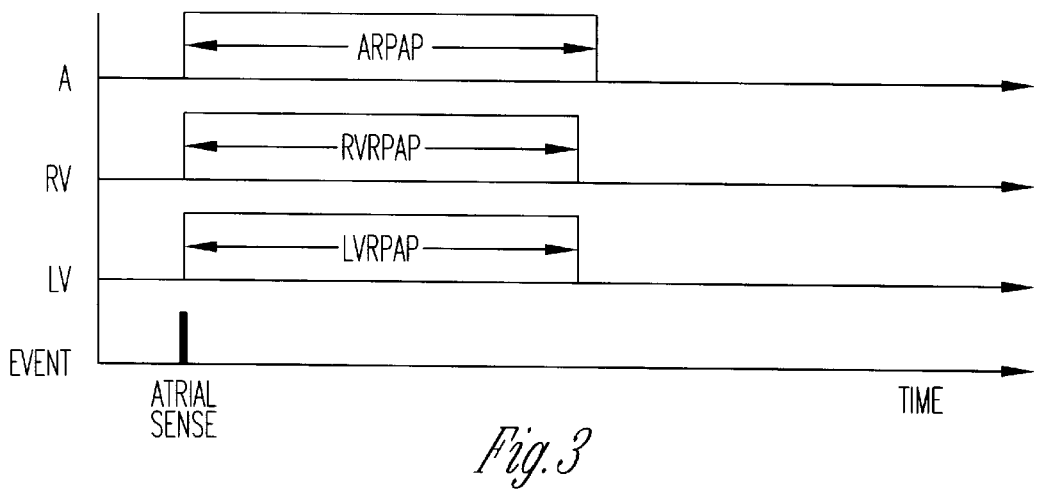
FIG. 3 shows refractory periods following an atrial pace.

FIG. 3 depicts the refractory periods following an atrial pace. The atrial, right ventricular, and left ventricular channels are rendered refractory for selected intervals ARPAP, RVRPAP, and LVRPAP, respectively. Note that although RVRPAP and LVRPAP are shown as being equal, it may be advantageous to extend the left ventricular refractory period beyond the right ventricular refractory period in order to allow for the added time that a depolarization from a right atrial pace takes to reach the left atrium where it could possibly be oversensed by the left ventricular channel. There may also be instances where it would be advantageous to set the RVRPAP longer than the LVRPAP.

Figure 4:
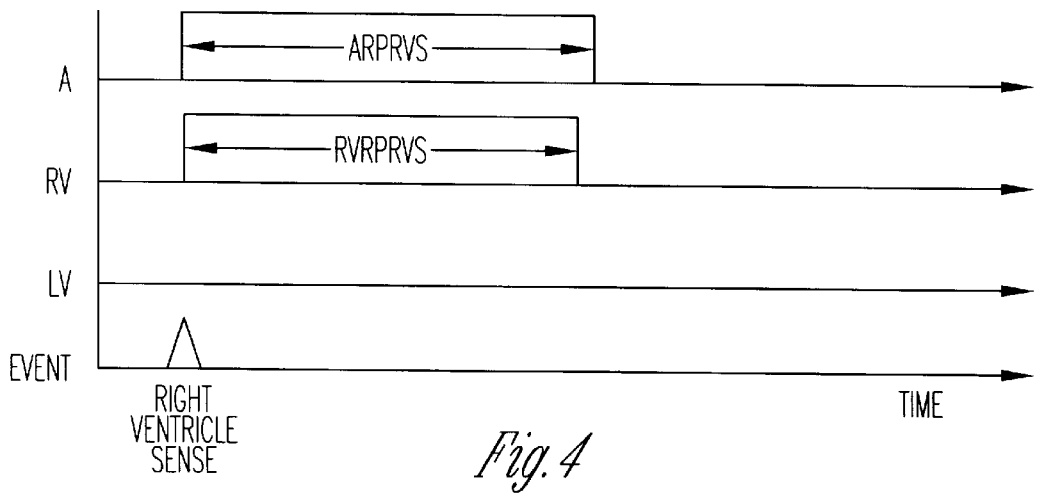
FIG. 4 shows refractory periods after a right ventricular sense.

FIG. 4 shows the sensing refractory periods after a sensed intrinsic right ventricular depolarization. The atrial and right ventricular channels are rendered refractory for separately selected intervals ARPRVS (which is commonly referred to as the post-ventricular atrial refractory period or PVARP, used primarily to prevent pacemaker mediated tachycardia) and RVRPRVS as is done for a conventional dual-chamber pacemaker with sensing only in the right ventricle. The left ventricular sensing channel remains non-refractory, however, in order to continue sensing for a depolarization which would inhibit a left ventricular pace output and to allow diagnostic functions in the cardiac rhythm management device to count the intrinsic left ventricular event. For left ventricular pacing in which the lower rate limit interval is controlled by right ventricular events (i.e., where pacing of either ventricle is inhibited by a right ventricular sense), it is desirable to provide a time interval triggered by a left ventricular sense signal during which pacing of the left ventricle is inhibited. That inhibitory interval, referred to herein as LVPP for left ventricular protective period, serves to prevent a left ventricular pace during the vulnerable period following a depolarization which in some patients can trigger ventricular arrhythmias.

Figure 5:
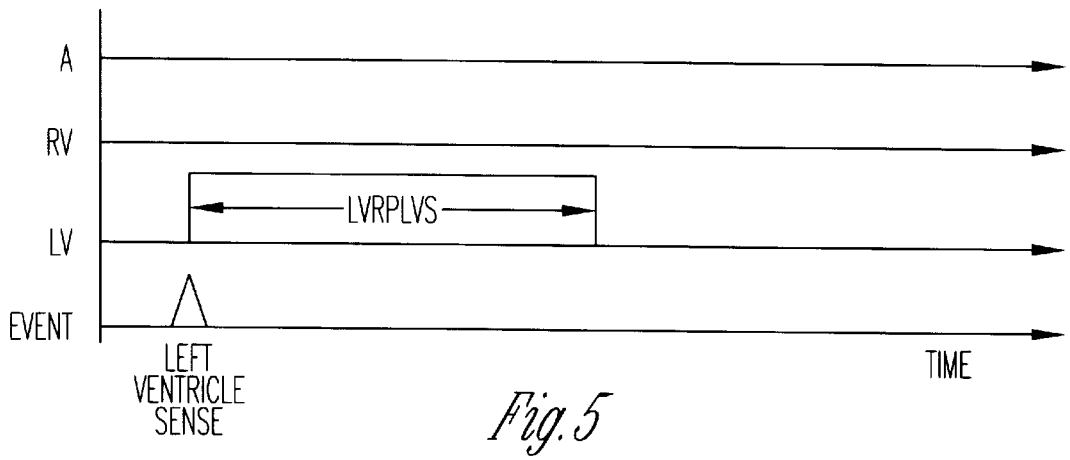
FIG. 5 shows refractory periods after a left ventricular sense.

FIG. 5 shows the refractory periods of the sensing channels following an intrinsic left ventricular event. Only the left ventricle channel is rendered refractory for a selected interval LVRPLVS. In order not to impact pacing algorithms dependent upon right ventricular and atrial events, it is advantageous to not initiate refractory periods in either of these sensing channels. Note that an LVPP interval may also be triggered by the left ventricular sense.

FIGS. 6 through 10 show the refractory periods of the sensing channels after ventricular pace events when the pacemaker is operated in biventricular pace mode with no ventricular triggering. In this mode, ventricular pacing is triggered by an atrial sense after expiration of the AVI or expiration of the LRL interval. In either case, ventricular pacing is inhibited by a right ventricular sense. A left ventricular pace is output offset from a right ventricle pace by a biventricular offset interval BVD (i.e., a synchronized chamber offset interval). The interval BVD may be zero in order to pace both ventricles simultaneously, positive in order to pace the left ventricle after the right, or negative if the left ventricle is paced before the right.

Figure 6:
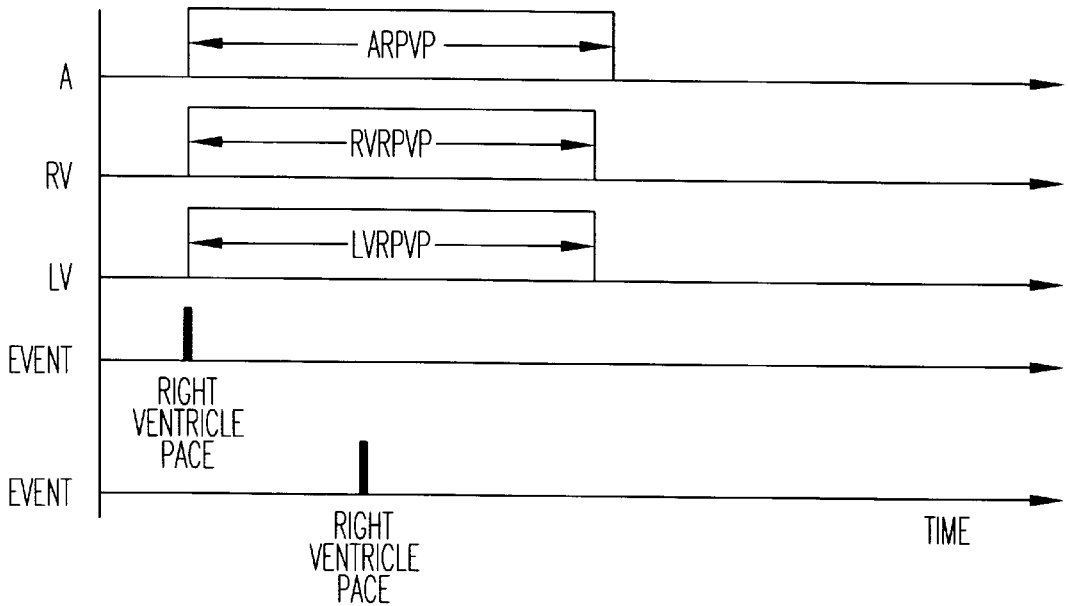
FIGS. 6 and 12 shows refractory periods following a ventricular pace in biventricular pacing mode with a positive biventricular delay.
Figure 8:
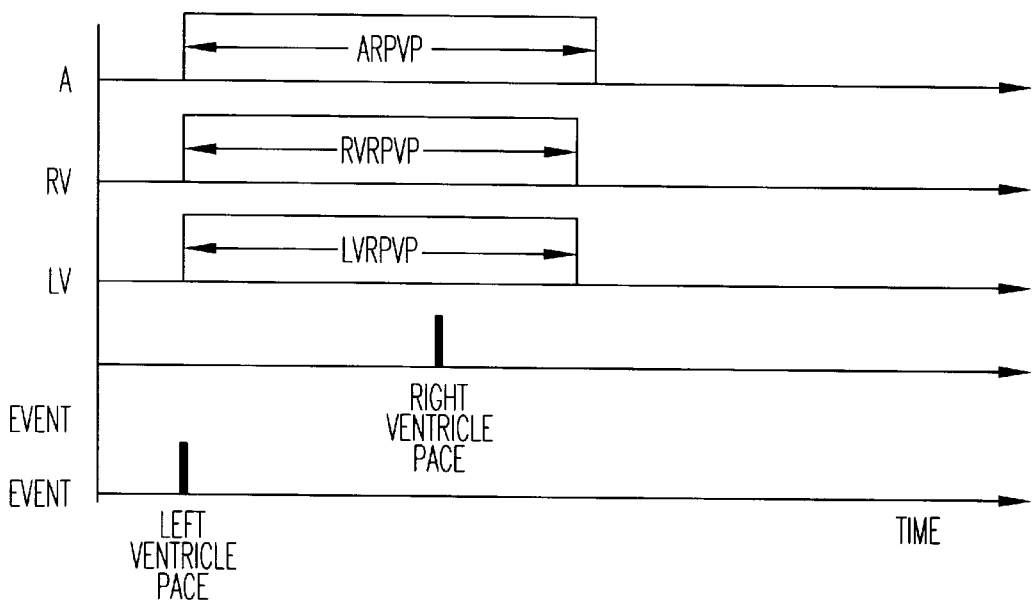
FIGS. 8 and 11 shows refractory periods periods following a ventricular pace in biventricular pacing mode with a negative biventricular delay.
Figure 10:
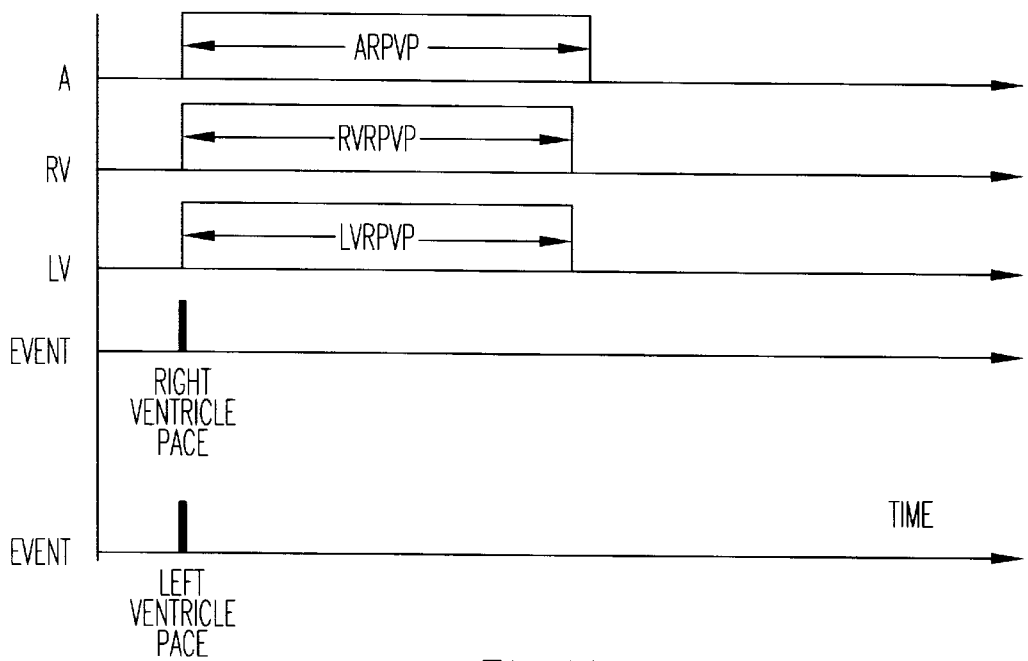
FIG. 10 shows refractory periods following a ventricular pace in biventricular pacing mode with simultaneous ventricular pacing.

FIG. 6 shows the pacing refractory periods defined by intervals ARPVP, RVRPVP, and LVRPVP for the atrial, right ventricular, and left ventricular channels, respectively, after a biventricular pace with a positive BVD. Intervals ARPVP, RVRPVP and LVRPVP start at the instant of the right ventricular pace. It should be noted that, in order to prevent sensing the depolarization produced by the pace, the left ventricular channel should be rendered refractory following a right ventricle pace for a period of time long enough to encompass the time it takes for a depolarization wave to reach the left ventricle. The right to left ventricle conduction time may be short enough so that no additional refractory time is needed following the left ventricular pace which occurs after the delay interval BVD. However, it may be advantageous to maintain a minimum interval MINREF from the left ventricular pace to the end of the RVRPVP and LVRPVP. This means that pacing refractory intervals for the atrial and both ventricular sensing channels in biventricular pacing mode can be defined so as to be triggered by whichever ventricular pace occurs first. Thus both RVRPVP and LVRPVP can be triggered by the right ventricular pace when BVD is positive. FIG. 8 shows the refractory periods for biventricular pacing mode in which the left ventricle is paced first followed by a right ventricular pace after a selected biventricular delay interval BVD (i.e., BVD is negative). The refractory period intervals ARPVP, RVRPVP, and LVRPVP for the atrial and ventricular channels are similar to those of FIG. 6 except that they are triggered by a left ventricular pace. FIG. 10 shows the refractory periods in biventricular pacing mode with the ventricles paced simultaneously (i.e., when BVD is zero) again showing the intervals ARPVP, RVRPVP, and LVRPVP triggered by either of the ventricular paces.

Figure 11:
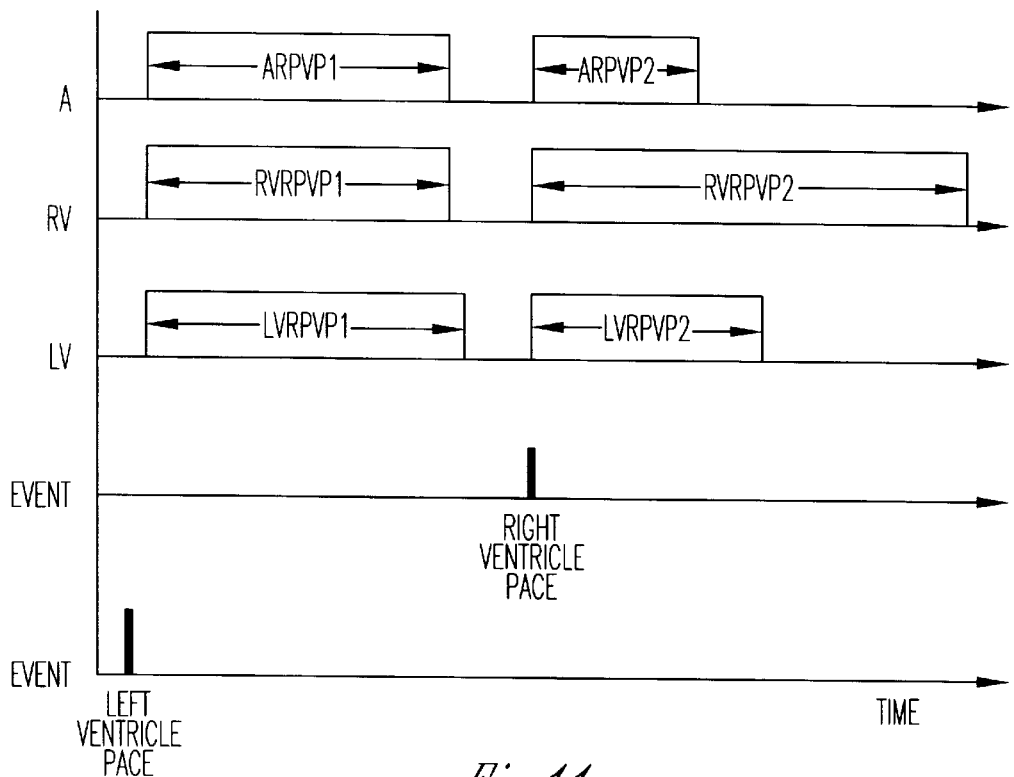
Figure 12:
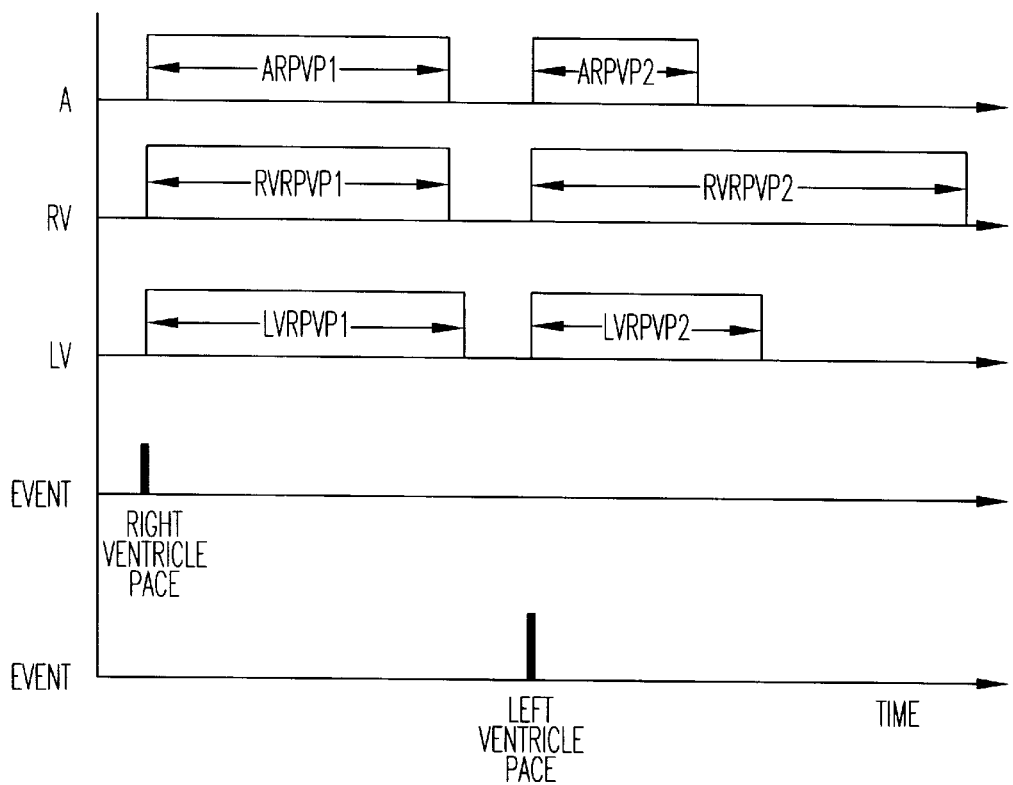

In another embodiment, during biventricular pacing with a non-zero BVD, the refractory periods for the atrium and ventricles are started on the last ventricular pace. This is depicted in FIGS. 11 and 12. As shown, refractory periods ARPVP1, RVRPVP1, and LVRPVP1 are triggered by the leading ventricular pace. The lagging ventricular pace triggers refractory periods ARPVP2, RVRPVP2, and LVRPVP2. If any of the ARPVP1, RVRPVP1, or LVRPVP1 periods exceed the BVD, that refractory period is truncated at the time of the lagging ventricular pace. The ARPVP1, RVRPVP1, and LVRPVP1 periods may be the same or different as the ARPVP2, RVRPVP2, and LVRPVP2 periods.

Figure 7:
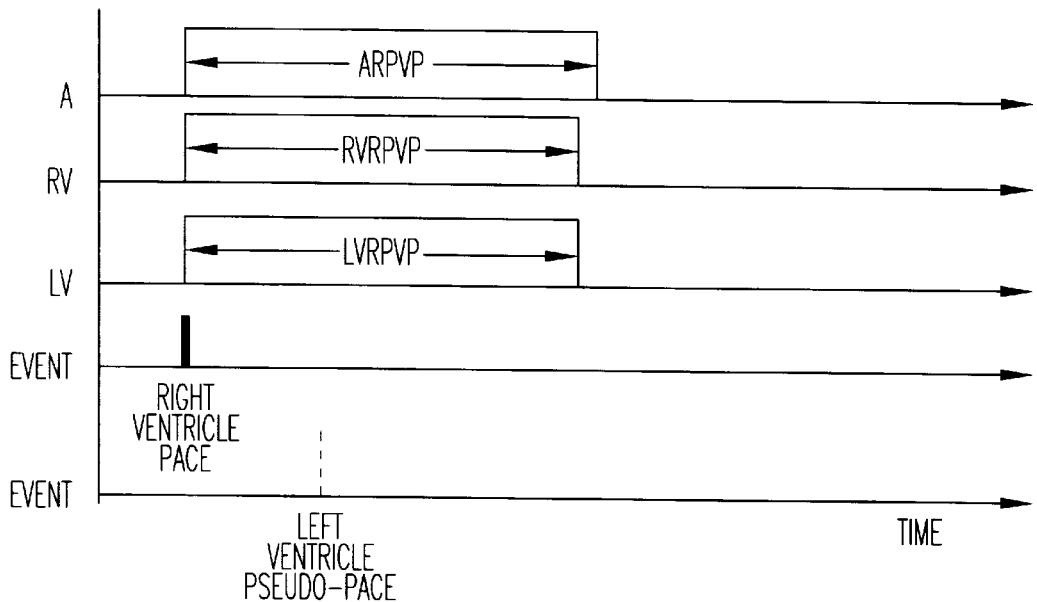
FIG. 7 shows refractory periods following a ventricular pace in biventricular pacing mode with a positive biventricular delay where the left ventricular pace is inhibited.
Figure 9:
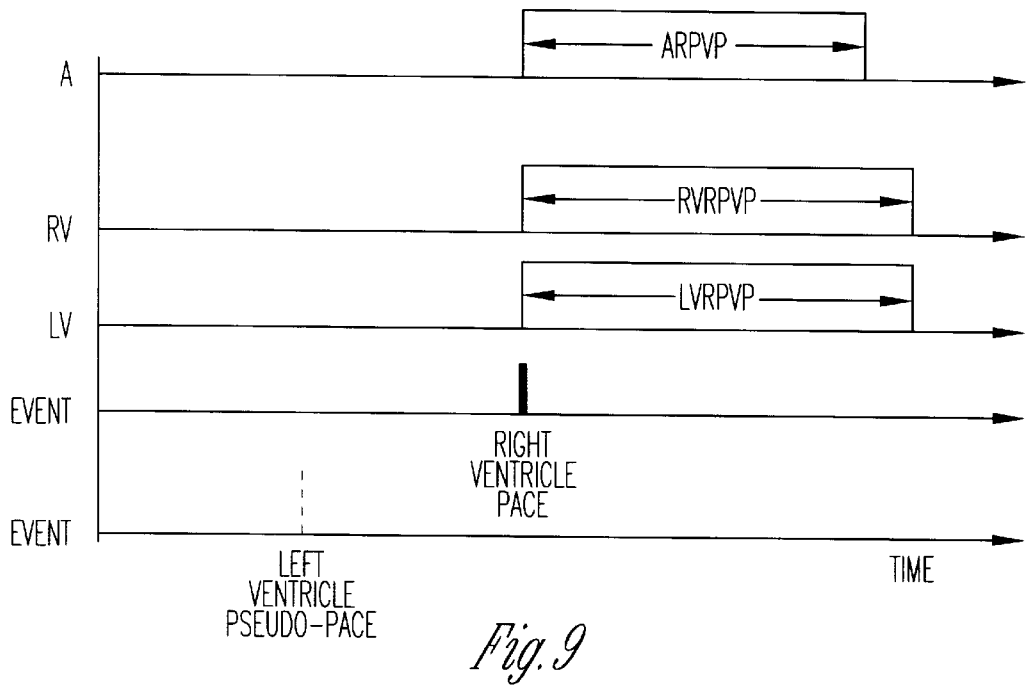
FIG. 9 shows refractory periods following a ventricular pace in biventricular pacing mode with a negative biventricular delay where the left ventricular pace is inhibited.

In any of the non-ventricular-triggered biventricular pacing modes, the left ventricular pace is inhibited if the pace would fall within the left ventricular protective period interval LVPP. The LVPP may be triggered by a left ventricular sense occurring before the right ventricular pace (i.e., before the onset of the left ventricular refractory period). In that event, as shown in FIG. 7 with respect to a biventricular pacing mode with a positive BVD, the refractory intervals are triggered by the right ventricular pace and are left unchanged from those of FIG. 6. The event labeled as a left ventricular pseudo-pace represents where the left ventricular pace would have occurred were it not inhibited. FIG. 9 shows that the refractory intervals are triggered by the right ventricular pace when the right ventricular pace is to follow the left ventricular pace (i.e., BVD is negative) but no left ventricular pace occurs due to triggering of the LVPP. The pacing refractory periods with simultaneous ventricular pacing are similarly unchanged when left ventricular pacing is inhibited. Thus the earliest ventricular pace output occurring can be used to trigger the pacing refractory periods regardless of the value of the biventricular delay and whether or not the left ventricular protective period is triggered. In another embodiment, the refractory periods are triggered by the right ventricular pace but set to a value different than that used during biventricular pacing.

Figure 13:
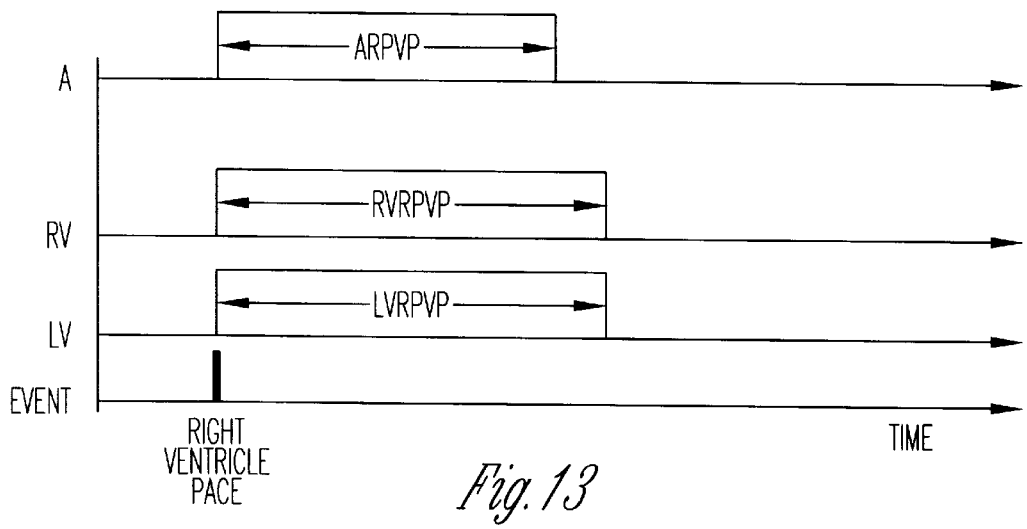
FIG. 13 shows refractory periods following a ventricular pace in a right ventricle-only pacing mode.
Figure 14:
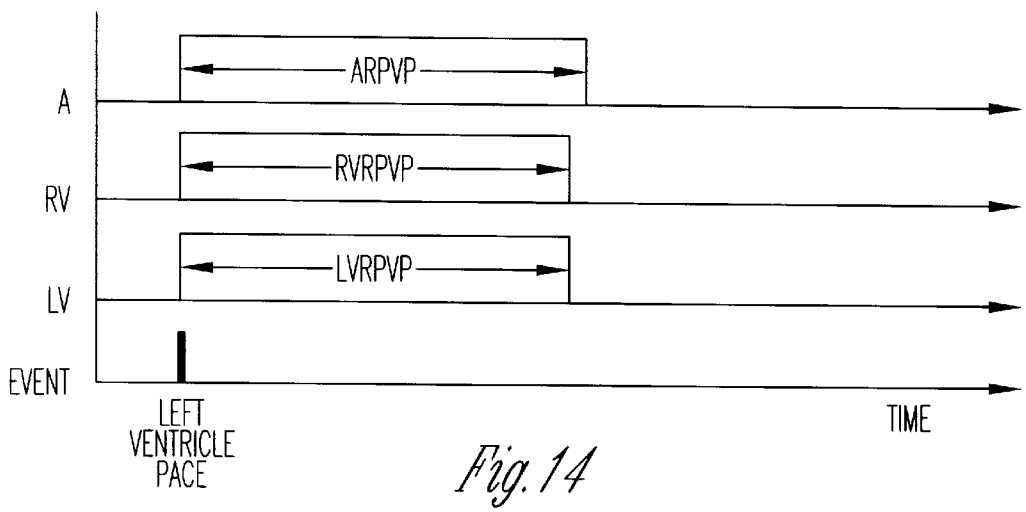
FIG. 14 shows refractory periods following a ventricular pace in a left ventricle-only pacing mode.
Figure 15:
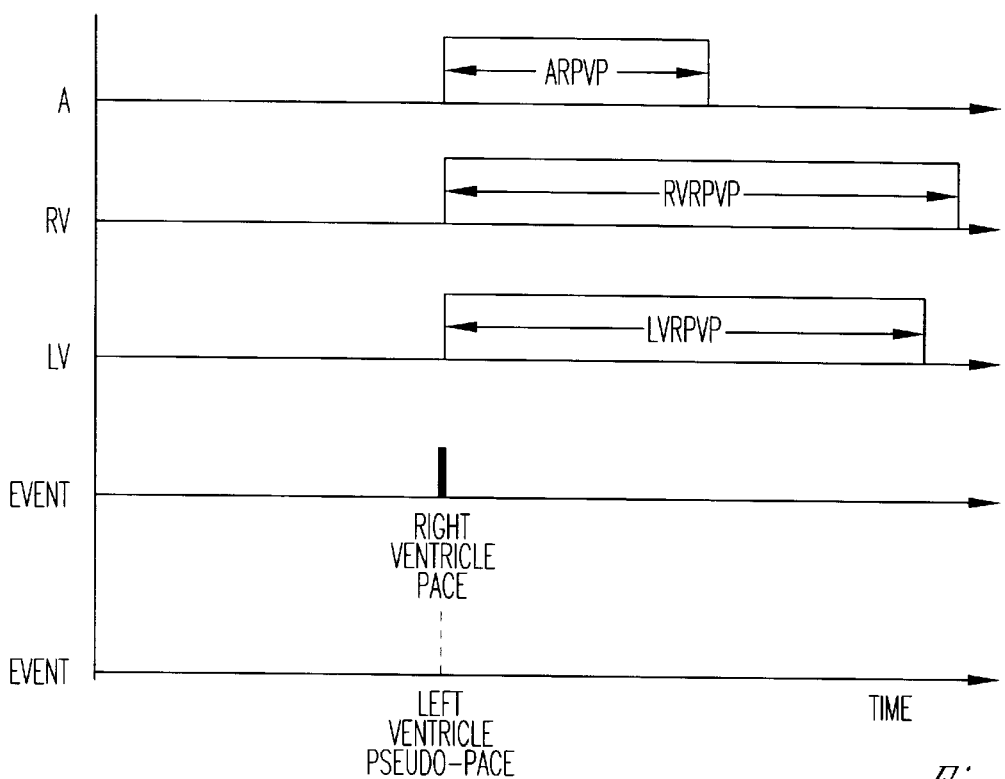
FIG. 15 shows refractory periods following a right ventricular safety pace.

In some situations, the best hemodynamic effect may result from pacing only the right or left ventricle. FIGS. 13 and 14 depict the refractory periods associated with right-only and left-only ventricular pacing, respectively. During left-only ventricular pacing, the left ventricular paces are inhibited by either left ventricular or right ventricular sensed events. FIG. 15 depicts the refractory periods after a right ventricular safety pace delivered during left ventricle-only pacing when the left ventricle pace is inhibited by an LVPP. During right-only ventricular pacing, right ventricular paces are inhibited by only right ventricular sensed events. Since left ventricular sensing may still be used for purposes other than pace inhibition, such as diagnostic counting of left ventricular senses, implementation of a refractory period for the left ventricular sensing channel may be necessary while in a right-only ventricular pacing mode. As shown in FIGS. 13, 14, and 15, all refractory periods ARPVP, RVRPVP, and LVRPVP start at the instant of the right ventricular pace in the case of right-only ventricular pacing, and at the instant of the left ventricular pace in the case of left-only ventricular pacing.

Figure 16:
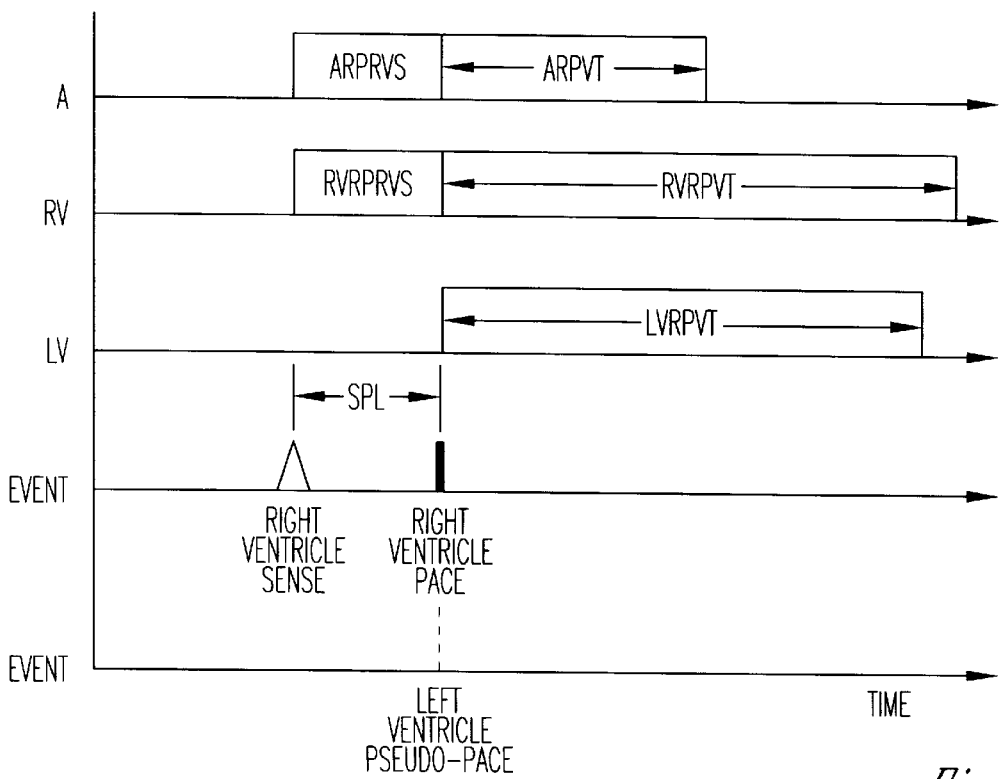
FIG. 16 shows refractory periods for ventricular triggered biventricular pacing with inhibition of the left ventricular pace.
Figure 17:
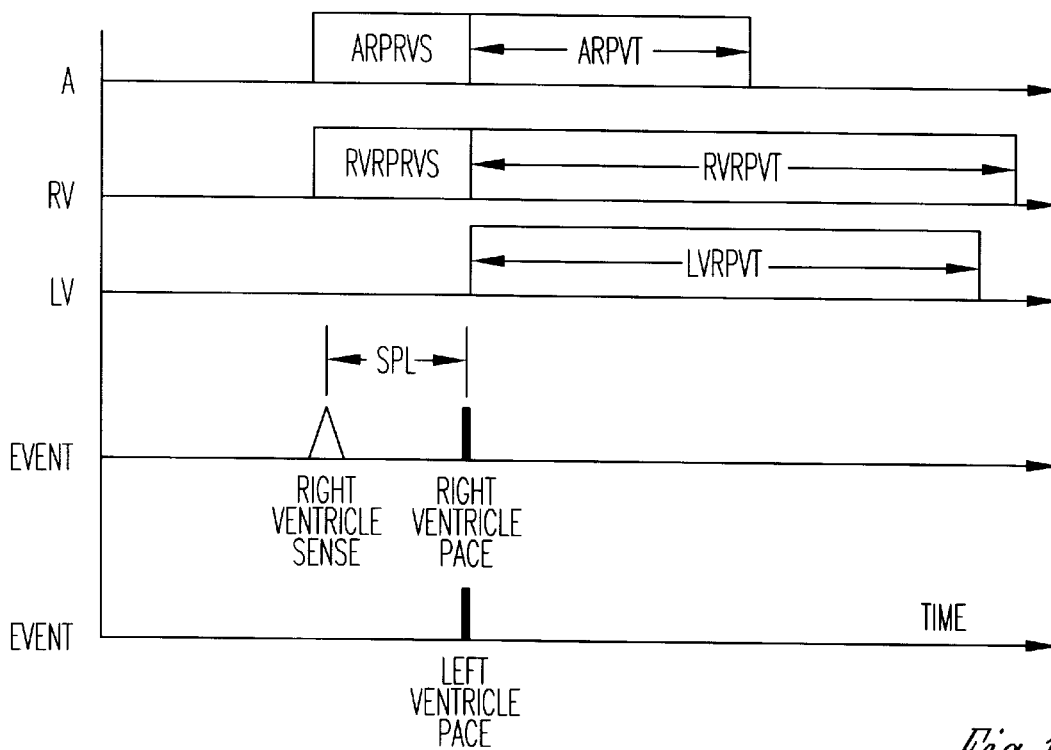
FIG. 17 shows refractory periods for ventricular triggered biventricular pacing where both ventricles are paced.
Figure 18:
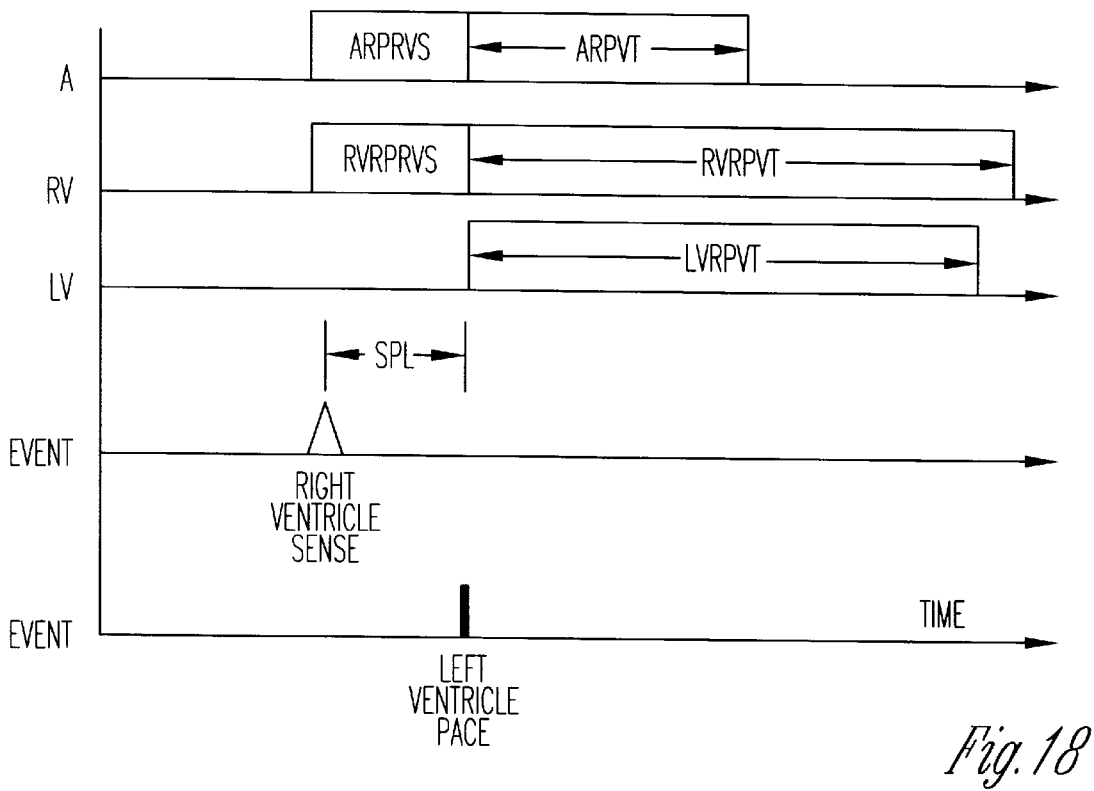
FIG. 18 shows refractory periods for ventricular triggered left ventricle-only pacing.

FIGS. 16, 17, and 18 show the refractory intervals of the sensing channels when the pacemaker is operated in biventricular pacing mode with ventricular triggering. In this mode, rather than inhibiting pacing upon receipt of a right ventricular sense, ventricular pacing is triggered to occur in the shortest time possible after the sense in order to produce a coordinated contraction of the ventricles. This mode of pacing may be desirable when the inherent intraventricular conduction time of the heart is long enough that the pacemaker is able to reliably insert a pace before depolarization from the right ventricle would reach the left ventricle. The time delay between a right ventricular sense and the ensuing pace output is dictated by the response time of the hardware and is designated in FIGS. 16, 17, and 18 by the sense to pace latency interval SPL. The mode may operate such that following a right ventricular sense, either the left ventricle only is paced as shown in FIGS. 16 and 18, or both ventricles are paced as shown in FIG. 17. In the latter case, the right ventricle is paced even though a right ventricular sense has been received to allow for the possibility that the right ventricular sense was actually a far-field left ventricular sense in the right ventricular channel. If the right ventricular sense were actually from the right ventricle, the right ventricular pace would occur during the right ventricle's physiological refractory period and be of no consequence. With either type of ventricular triggered biventricular pacing mode, pacing of the left ventricle is inhibited if it would be delivered during the LVPP interval. FIGS. 16, 17, and 18 show that in ventricular triggered mode, separately selectable refractory period intervals ARPVT, RVRPVT, and LVRPVT for the atrial and ventricular sensing channels are triggered by either a univentricular or biventricular pace. FIGS. 16, 17, and 18 also show that the right ventricle and atrium are refractory during the SPL. The atrial and right ventricular refractory periods during the SPL (ARPRVS, RVRPRVS) are triggered by the right ventricular sense and are truncated at the time of the ventricular pace.

Although the invention has been described in conjunction with the foregoing specific embodiment, many alternatives, variations, and modifications will be apparent to those of ordinary skill in the art. Such alternatives, variations, and modifications are intended to fall within the scope of the following appended claims.

What is claimed is:

1. A method for operating a cardiac rhythm management device, comprising:

sensing a rate chamber and a synchronized chamber through separate channels and generating sense signals upon detection of depolarization occurring in a chamber;

pacing the synchronized chamber upon expiration of an escape interval without receipt of a rate chamber sense signal from the rate chamber sensing channel;

rendering each sensing channel refractory for a separately selected pacing refractory period after a pacing event; and, rendering a sensing channel refractory for a selected sensing refractory period after receipt of a sense signal from that channel while continuing to sense in the other channel.

2. The method of claim 1 wherein the rate and synchronized chambers are ventricles, designated as the ventricular rate chamber and the ventricular synchronized chamber.

3. The method of claim 2 further comprising;

sensing an atrium through a separate atrial channel and generating an atrial sense signal upon detection of depolarization occurring in the atrium;

pacing a ventricle upon expiration of a selected atrioventricular time interval without receipt of a ventricular rate chamber sense signal from the ventricular rate chamber sensing channel, where the atrioventricular time interval starts with receipt of an atrial sense signal;

rendering the atrial sensing channel refractory for a selected pacing refractory period after a ventricular pacing event; and, rendering the atrial sensing channel refractory for a selected sensing refractory period after a ventricular rate chamber sensing signal but continuing to sense in the atrial channel following a ventricular synchronized chamber sensing signal.

4. The method of claim 3 further comprising:

pacing an atrium upon expiration of a selected atrial escape interval without receipt of an atrial sense signal, where the atrial escape interval starts with either receipt of a ventricular rate chamber sense signal or a ventricular pacing event; and, rendering the atrial and both ventricular sensing channels refractory for separately selected periods of time after an atrial pacing event.

5. The method of claim 3 further comprising rendering the atrial sensing channel refractory for a selected period of time after an atrial sense.

6. The method of claim 3 further comprising rendering the ventricular synchronized chamber sensing channel refractory for a selected period of time after an atrial sense.

7. The method of claim 1 wherein the rate and synchronized chambers are atria.

8. The method of claim 1 wherein the rate and synchronized chambers are sensing/pacing sites in the same heart chamber.

9. The method of claim 1 further comprising sensing a plurality of synchronized sensing/pacing sites in the synchronized chamber through separate channels and generating sense signals upon detection of depolarization occurring at each site.

10. The method of claim 9 further comprising pacing a plurality of synchronized sensing/pacing sites in the synchronized chamber through separate channels.

11. The method of claim 1 further comprising pacing the rate chamber upon expiration of an escape interval without receipt of a rate chamber sense signal from the rate chamber sensing channel.

12. The method of claim 1 wherein the rate and synchronized chambers are ventricles designated as the rate ventricle and synchronized ventricle, respectively, and further comprising:

sensing an atrium through a separate atrial channel and generating an atrial sense signal upon detection of depolarization occurring in the atrium; and, wherein the escape interval is an atrioventricular interval which starts with receipt of an atrial sense signal.

13. The method of claim 1 further comprising pacing both chambers upon expiration of an escape interval without receipt of a rate chamber sense signal from the rate chamber sensing channel.

14. The method of claim 13 wherein the chambers are paced with a selected synchronized chamber channel offset interval.

15. The method of claim 14 wherein the pacing refractory period of each chamber begins with pacing of the earlier paced chamber.

16. The method of claim 15 wherein a minimum refractory period is maintained in the later paced chamber after the later pace.

17. The method of claim 1 wherein a sense in one chamber triggers a pace in the other chamber.

18. The method of claim 17 wherein the pacing refractory period of both chambers begins when the paced chamber receives the pace.

19. A cardiac rhythm management device, comprising:

separate sensing channels for sensing a rate chamber and a synchronized chamber and generating sense signals upon detection of depolarization occurring in a chamber;

a pacing channel for delivering pacing pulses to the synchronized chamber upon expiration of an escape interval without receipt of a rate chamber sense signal from the rate chamber sensing channel;

a controller for controlling the delivery of paces in accordance with a programmed pacing mode;

a pacing refractory period timer for rendering each sensing channel refractory for a selected period of time after a pacing event; and, a sensing refractory period timer for rendering the rate chamber sensing channel refractory for a selected period of time after receipt of a rate chamber sense signal without affecting the synchronized chamber sensing channel.

20. The device of claim 19 wherein the rate and synchronized chambers are ventricles, designated as the ventricular rate chamber and the ventricular synchronized chamber.

21. The device of claim 20 further comprising;

an atrial sensing channel for sensing atrial depolarizations and generating atrial sense signals in accordance therewith;

an atrioventricular timer for triggering a ventricular pace upon expiration of a selected atrioventricular time interval without receipt of a ventricular rate chamber sense signal from the ventricular rate chamber sensing channel, where the atrioventricular timer is reset upon receipt of an atrial sense signal;

a refractory period timer for rendering the atrial sensing channel refractory for a selected pacing refractory period after a ventricular pacing event; and, a refractory period timer and logic circuitry for rendering the atrial sensing channel refractory for a selected sensing refractory period after a ventricular rate chamber sensing signal, wherein the atrial sensing channel continues to sense following a ventricular synchronized chamber sensing signal.

22. The device of claim 21 further comprising:

an atrial pacing channel for delivering paces to an atrium;

wherein the controller is programmed to deliver paces to the atrium in accordance with an atrial pacing mode; and, pacing refractory period timers for rendering the atrial and both ventricular sensing channels refractory for selected refractory periods after an atrial pacing event.

23. The device of claim 19 wherein the rate and synchronized chambers are atria.

24. The device of claim 19 wherein the rate and synchronized chambers are sensing/pacing sites in the same heart chamber.

25. The device of claim 19 further comprising separate channels for sensing a plurality of synchronized sensing/pacing sites in the synchronized chamber and generating sense signals upon detection of depolarization occurring at each site.

26. The device of claim 19 further comprising separate channels for pacing a plurality of synchronized sensing/pacing sites in the synchronized chamber.

27. The device of claim 19 further comprising a second pacing channel for delivering paces to the rate chamber.

28. The device of claim 27 wherein the controller is programmed to pace one chamber upon expiration an escape interval and pace the other chamber within a selected synchronized chamber offset interval.

29. The device of claim 28 wherein the pacing refractory period timer for each chamber is reset upon pacing of the earlier paced chamber.

30. The device of claim 28 wherein the pacing refractory period timers for both ventricles are reset upon pacing of the earlier paced ventricle.

31. The device of claim 27 wherein the controller is programmed to pace the synchronized chamber within a latency period after receipt of a rate chamber sense signal.

32. The device of claim 31 wherein the pacing refractory period timers for both chambers are reset after the pace is delivered.

33. The device of claim 27 wherein the controller is programmed to pace both chambers within a latency period after receipt of a rate chamber sense signal.

* * * * *